United States Patent [19]
Ellis et al.

[11] Patent Number: 6,043,070
[45] Date of Patent: Mar. 28, 2000

[54] PHOSPHORAMIDATE-PHOSPHODIESTER OLIGONUCLEOTIDE CHIMERA AS PRIMERS

[75] Inventors: Nicole M. Ellis, San Mateo; Robert G. Kuimelis, Redwood City; Cheryl R. Heiner, La Honda; Katherine D. Lazaruk, Redwood City; Patric Sean Walsh, Danville, all of Calif.

[73] Assignee: The Perkin-Elmer Corporation

[21] Appl. No.: 08/924,031

[22] Filed: Aug. 29, 1997

[51] Int. Cl.⁷ .............................. C12N 9/10; C07H 21/04
[52] U.S. Cl. .............................. 435/193; 436/501; 435/6; 435/91.2; 536/22.1; 536/24.33
[58] Field of Search .............................. 435/6, 91.2, 810, 435/193; 436/501; 536/23.1, 22.1, 24.1, 24.3–33; 935/77, 78

[56] References Cited

U.S. PATENT DOCUMENTS 5,475,925 12/1995 Letsinger et al. .

FOREIGN PATENT DOCUMENTS

| 0747479 | 12/1996 | European Pat. Off. ........ C12N 15/10 |
| WO 96/13611 | 5/1996 | WIPO .............................. C12Q 1/68 |
| WO 96/37630 | 11/1996 | WIPO .............................. C12Q 1/68 |
| WO 97/16566 | 5/1997 | WIPO .............................. C12Q 1/68 |
| WO 97/31009 | 8/1997 | WIPO .............................. C07H 21/00 |

OTHER PUBLICATIONS

Uhlmann et al., Chemical Reviews, vol. 90, No. 4, pp. 544–584, 1990.
Sommer et al., Nucleic Acids Research, vol. 17, No. 16., p. 6749, 1989.
Peyrottes et al., "Oligodeoxynucleoside phosphoramidates (P–$NH_2$): synthesis and thermal stability of duplexes with DNA and RNA targets," *Nucelic Acids Research* 24(10):1841–1848 (1996).

*Primary Examiner*—Ardin H. Marschel
*Attorney, Agent, or Firm*—Scott R. Bartner

[57] ABSTRACT

The invention relates to novel chimeric phosphoramidate oligonucleotides and their use in primer-extension methods such as DNA sequencing and nucleic acid amplification. The subject chimeric phosphoramidate oligonucleotides have both N3'-phosphoramidate linkages and phosphodiester linkages. The invention includes methods of primer extension using the subject chimeric oligonucleotides as primers. Primer extension methods of interest include nucleic acid amplification reactions, e.g. PCR, and polynucleotide sequencing reactions. In the primer extension methods of the invention, a chimeric phosphoramidate oligonucleotide primer is annealed to a polynucleotide template. After annealing, the chimeric oligonucleotide primer is extended by joining a nucleotide to the 3' end of the primer by a DNA polymerase catalyzed reaction. Other embodiments of the invention include methods of primer extension using phosphoramidate linkage containing polynucleotide templates. Such methods include annealing an oligonucleotide primer (chimeric or otherwise) to a polynucleotide template comprising at least one phosphoramidate linkage. Nucleotides are added to the primer in a DNA polymerase catalyzed reaction. Primer extension takes place across one or more of the phosphoramidate linkages in the template. The invention includes compositions comprising a chimeric phosphoramidate oligo-nucleotide of the invention and a divalent cation. Divalent cations serve to increase the binding affinity between the chimeric oligonucleotides of the invention and a polynucleotide template. Additionally, divalent cations may be used to stabilize the phosphoramidate linkages of the subject chimeric oligonucleotides against hydrolysis at elevated temperatures, such as the temperatures used in PCR and cycle sequencing. The subject compositions may further comprise a thermostable DNA polymerase such as Taq DNA polymerase.

7 Claims, 1 Drawing Sheet

PHOSPHORAMIDATE-PHOSPHODIESTER OLIGONUCLEOTIDE CHIMERA AS PRIMERS

BACKGROUND

A key factor in the recent advances in molecular biology has been the use of oligonucleotide analogs to study and enable basic cellular processes, including the regulation of gene expression. One of the most powerful and versatile tools in molecular biology is the in vitro replication of nucleic acid sequences, as exemplified by the ubiquitous practice and commercial value of the polymerase chain reaction (PCR) and DNA sequencing. Both methods entail hybridization of a primer, usually a short (15–30 nt) synthetic oligonucleotide, to a single-stranded template nucleic acid. A polymerase enzyme catalyzes extension, i.e., polymerization, from the 3' terminus of the primer with 5' triphosphate nucleotides complementary to the template strand. By this general replication method, sequencing information may be generated, or amplification of the template may be achieved through the choice of selected variables such as primers, multiple primers, enzymes, nucleotides, and the selection of buffers, salts, temperature, and temperature cycling conditions.

Many internucleotide analogs of DNA have been synthesized, primarily for study of their antisense effects, the inhibition of gene expression at the transcriptional level, targeting DNA, or more commonly pre-translational, targeting mRNA. The antisense effect includes occupying a critical gene expression site in a sequence-specific effect with a high-affinity, nuclease-resistant oligonucleotide analog or the RnaseH mediated cleavage of mRNA in the duplex formed with the antisense oligonucleotide. The latter effect results in destruction of genetic message. Both strategies have the intended effect of precluding formation of the undesired gene product, typically of viral origin.

Internucleotide DNA analogs with a bridging nitrogen, especially replacing the oxygen at the 3' of the deoxyribose moieties, have markedly different physical properties when compared with DNA. These DNA analogs having nitrogen replacement of oxygen at the 3' deoxyribose moiety are commonly referred to as phosphoramidates (Gryaznov et al., Nuc. Acids Res. 24:1508–1514 (1996). Phosphoramidate containing oligonucleotides have been shown to have greater affinity for their complementary DNA and RNA, exemplified by higher thermal melting values, $T_m$. In this effect, affinity is synonymous with hybridization strength and duplex stability. Phosphoramidate oligonucleotides demonstrate a high degree of base-discrimination to pair with a complementary strand following the normal Watson-Crick rules. The level of discrimination is often termed specificity. Affinity may be measured in experiments that compare the $T_m$ values of duplexes having perfect Watson-Crick complementarity versus those with one or more mismatches. The destabilization, seen by the decrease in $T_m$, is a measure of specificity, pertinent to structural modifications, hybridization conditions, or other experimental parameters.

Additionally, phosphoramidate oligonucleotides may form triple helical structures, involving three strands in a sequence dependent manner. Triplex structures can result from directly targeting double-stranded DNA with phosphoramidate oligonucleotides. Phosphoramidate oligonucleotides are poor substrates for phosphodiesterase, exo- and endonucleases which rapidly degrade foreign DNA in cells. Thus, such analogs may exert their antisense and other hybridization-dependent effects, over a useful period of time in vitro or in vivo.

Although many DNA analogs have some desirable properties, such analogs may have numerous other properties that render them unsuitable for common molecular biology techniques such as PCR or nucleic acid sequencing. For example, peptide nucleic acid (PNAs) cannot serve as replication template or function as synthesis primers. Similarly, DNA analogs having only phosphoramidate linkages between nucleosides have been found not to function as synthesis primers.

Accordingly, it is of interest to provide new polynucleotide analogs that have one or more properties that are advantageous with respect to corresponding DNA molecules, but may also be used in a variety of molecular biology methods including PCR and other primer extension reactions. It is also of interest to provide methods of using such analogs.

SUMMARY

The invention relates to novel chimeric phosphoramidate oligonucleotides and their use in primer-extension methods such as DNA sequencing and nucleic acid amplification. The subject chimeric phosphoramidate oligonucleotides have both N3'-phosphoramidate linkages and phosphodiester linkages. At least one of the phosphodiester linkages is at the 3' end of the chimeric oligonucleotide primer. The chimeric phosphoramidate oligonucleotide is of sufficient length to hybridize to a template polynucleotide of interest.

Surprising aspects of embodiments of the invention include the discovery that phosphoramidate linkage containing oligonucleotides could be used as primers for extension. The chimeric oligonucleotides of the invention may, in many embodiments of primer extension assays, produce surprisingly large product yields. Moreover, the sucessful use of phosphoramidate linkage containing oligonucleotides as primers for thermostable DNA polymerases, particularly Taq DNA polymerase and derivatives thereof, was unexpected. Yet another surprising aspect of the invention was the discovery that phosphoramidate linkage containing polynucleotides could be used as templates in primer extension reactions, e.g., PCR.

The invention includes chimeric phosphoramidate linkage containing oligonucleotides that may be used as primers for polynucleotide synthesis. One embodiment of the invention is a chimeric phosphoramidate oligonucleotide according to the formula:

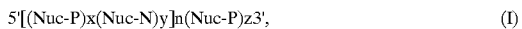

5'[(Nuc-P)x(Nuc-N)y]n(Nuc-P)z3',  (I)

wherein n≧0, x≧0, y≧1, and z≧1. The chimeric phosphoramidate oligonucleotide is of sufficient length to hybridize to a template polynucleotide of interest.

Another embodiment of the invention is a composition comprising a chimeric phosphoramidate oligonucleotide of the invention and a divalent cation. Divalent cations serve to increase the binding affinity between the chimeric oligonucleotides of the invention and a polynucleotide template much more than would be expected based on the effects of divalent cations observed with oligonucleotides containing only phosphodiester linkages, i.e., DNA. Additionally, divalent cations may be used to stabilize the phosphoramidate linkages of the subject chimeric oligonucleotides against hydrolysis at elevated temperatures, such as the temperatures used in PCR and cycle sequencing. The subject compositions may further comprise a thermostable DNA polymerase such as Taq DNA polymerase.

Other embodiments of the subject invention include methods of primer extension using the subject chimeric oligonucleotides as primers. Primer extension methods include nucleic acid amplification reactions, e.g., PCR, and polynucleotide sequencing reactions. In the primer extension methods of the invention, a chimeric phosphoramidate oligonucleotide primer is annealed to a polynucleotide template. After annealing, the chimeric oligonucleotide primer is extended by joining a nucleotide to the 3' end of the primer by a DNA polymerase catalyzed reaction.

Other embodiments of the invention include methods of primer extension using phosphoramidate linkage containing polynucleotide templates. Such methods include the step of annealing an oligonucleotide primer (chimeric or otherwise) to a polynucleotide template comprising at least one phosphoramidate linkage. Nucleotides are added to the primer in a DNA polymerase catalyzed reaction. Primer extension takes place across one or more of the phosphoramidate linkages in the template.

Additional embodiments of the invention include method of suppressing non-templated terminal dA (nucleotide) addition by Taq DNA polymerase. The use of chimeric phosphoramidate oligonucleotides as primers for Taq DNA polymerase mediated reactions (including PCR) can reduce terminal dA addition by Taq or DNA polymerases with similar non-templated addition properties.

EMBODIMENTS OF THE INVENTION

Figure 1:
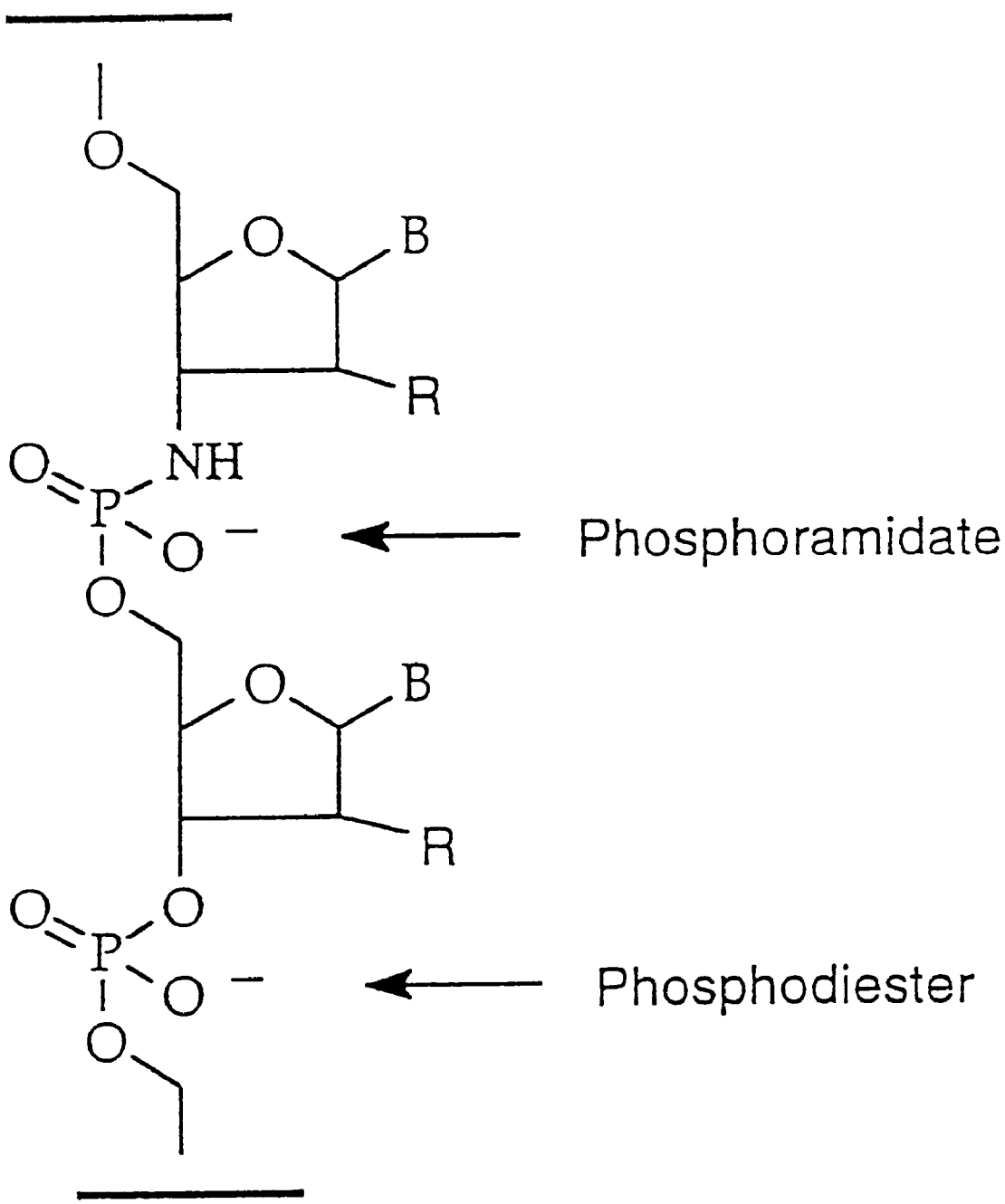
FIG. 1. This FIGURE is a diagram of an internal portion of a chimeric phosphoramidate oligonucleotide. The phosphoramidate and phosphodiester linkages are indicated. B represents a nucleoside base. R represents a hydrogen, hydroxy, lower alkyl, halogen, amino, lower alkoxy, or lower alcohol.

The invention relates to novel chimeric phosphoramidate oligonucleotides and their use in primer-extension methods such as DNA sequencing and nucleic acid amplification. The subject chimeric phosphoramidate oligonucleotides have both 3'-N-phosphoramidate linkages and phosphodiester linkages. At least one of the phosphodiester linkages is at the 3' end of the chimeric oligonucleotide primer. The phosphoramidate linkages may be at any other location in the chimeric oligonucleotide, including the linkage at the 5' end. The chimeric phosphoramidate oligonucleotides of the invention may be used in a variety of primer extension reactions.

An internal portion of a chimeric phosphoramidate oligonucleotide molecule of the invention is given in FIG. 1. The 3'-N-phosphodiester linkage are indicated. B represents a nucleoside base. B may be a nucleoside bases found in DNA or RNA, e.g. cytosine, adenine, guanine, thymine, uracil, or analogs thereof such as 2,6 diaminopurine, hypoxanthine, pseudouridine, C-5-methyl cytosine, C-5-bromouridine, C-5-propyne cytosine, C-5-propyne uridine, 7-deazapurine, isocytosine, isoguanine, 2-thiopyrimidine, and the like. R, the 2' position of sugar (or a functional equivalent thereof), may be a hydrogen, hydroxy, lower alkyl, halogen, amino, lower alkoxy, or lower alcohol.

The chimeric phosphoramidate oligonucleotide primers of the invention may be represented by the following formula:

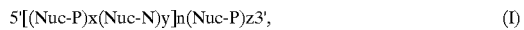

$$5'[(\text{Nuc-P})x(\text{Nuc-N})y]n(\text{Nuc-P})z3', \quad (I)$$

wherein $n \geq 0$, $x \geq 0$, $y \geq 1$, and $z \geq 1$. The primer is of sufficient length to hybridize to a polynucleotide template of interest. The hybridization may be specific or non-specific, depending upon the length and sequence of the primer as well as the sequence of the template of interest. Generally, the chimeric phosphoramidate oligonucleotide primers of formula I will comprise at least 5 nucleotide bases, more preferably at least 14 nucleotide bases, and even more preferably comprise at least 20 nucleotide bases. The primers may be considerably longer than 20 bases. Formula I is a schematic formula representative of the structure of the chimeric primers of the invention. The "5'" and "3'" in Formula I are used to denote the orientation of the linkages between the nucleosides that I the chimeric oligonucleotide.

The term "Nuc-P" refers to a nucleoside joined at the 5' end to the 3' end of a second nucleoside by a phosphodiester linkage. The 3' terminus of a compound of formula I is a hydroxy, so as to provide for extension of the primer in a polymerase catalyzed addition of a nucleotide.

The term "Nuc-N" refers to a nucleoside joined by a phosphoramidate linkage at the 3' end to the 5' end of a second nucleoside.

The term "n" in Formula I does not indicate that the Nuc-P and Nuc-N units located within the square brackets ("[" and "]") are necessarily a repeat unit. Instead, each "unit" denoted by the square brackets may be the same or different from one another. Thus, the 5' terminal nucleoside of compounds of Formula I may be joined to a second nucleoside by either a phosphodiester linkage or by a phosphoramidate linkage.

Although the chimeric phosphoramidate oligonucleotides of Formula I may have alternating phosphoramidate and phosphodiester linkages, in a preferred embodiment of the invention, the chimeric phosphoramidates oligonucleotides consists of (i) a first "block" of nucleosides joined by phosphoramidate linkages and (ii) a second "block" of nucleosides joined by phosphodiester linkages, wherein the block of nucleosides joined by phosphoramidate linkages is present on the 5' side of the chimeric oligonucleotide primer. The term "block" refers to 2 or more contiguous nucleosides. The blocks may contain the same or different numbers of bases.

The chimeric oligonucleotide primers of the invention may be synthesized using methods known to persons of ordinary skill in the art of organic chemistry. Methods of synthesizing phosphoramidate linkage containing oligonucleotides are described in, among other places, U.S. Pat. No. 5,631,135; U.S. Pat. No. 5,599,922; U.S. Pat. No. 5,591,607; Chen et al., *Nucleic Acids Res.* 23:2661–2668 (1996); Gryaznov et al., *Journal of the American Chem. Soc.* 116:3143–3144 (1994); Gryaznov et al., *Nucleic Acids Res.* 20:3403–3409 (1992); and Gryaznov et al., *Proc. Natl. Acad. Sci. USA*, 92:5798–5802 (1995), McCurdy et al., *Tet. Let.* 38:207–210 (1997). Chimeric oligonucleotides having phosphoramidate linkages and phosphodiester linkages may be synthesized by modifying the phosphoramidate synthesis process so as to introduce conventional phosphodiester linkages rather than phosphoramidate linkages.

Another embodiment of the invention is a composition (in aqueous solution) comprising a chimeric phosphoramidate oligonucleotide of Formula I and a divalent cation. Divalent cations have been found to enhance the stability of duplexes formed between the chimeric phosphoramidate oligonucleotides of Formula I and polynucleotide templates. The concentration of chimeric phosphoramidate oligonucleotide primers in the subject compositions may vary. Typically, the chimeric phosphoramidate oligonucleotide component of the composition is present in a concentration sufficient to enable the specific primer extension reaction of interest.

Such a concentration is often in the range of 0.1 μM to 1.0 μM. The subject compostions may be supplied in concentrated form so as to provide for stock solutions that may be conveniently diluted prior to use in primer extension reactions.

Suitable divalent cations for inclusion in the subject compositions include, but are not limited to, $Ca^{+2}$, $Mn^{+2}$, and $Mg^{+2}$. The divalent cation may be monoatomic or may contain multiple atoms. The divalent cations may be present in a concentration sufficient to increase the stability of the duplex. Very small amounts of divalent cations, i.e., any amount greater than zero, will increase stability of duplexes formed with the subject chimeric oligonucleotide primer and templates to some degree; however, preferred concentrations of divalent cation are in the range of 0.1 mM to 10 mM.

Divalent cations have also been found to protect the phosphoramidate linkages of the subject chimeric phosphoramidate oligonucleotides against hydrolysis at elevated temperatures, such as the denaturing temperatures used in PCR, cycle sequencing, or repeated rounds of the oligonucleotide ligation assay (U.S. Pat. No. 4,883,750). The use of the divalent cation $Mg^{+2}$ in those embodiments of the subject compositions designed for use at elevated temperatures is particularly preferred. In embodiments of the subject compositions employing $Mg^{+2}$ as the divalent cation, the $Mg^{+2}$ concentration is preferably in the range of 0.1 mM to 10 mM. In embodiments of the subject compositions employing $Mn^{+2}$ as the divalent cation, concentrations are preferably in the range of 0.1 mM to 10 mM. However, the effective concentrations of divalent cations for protection against hydrolysis at elevated temperatures will vary as a function of chimeric oligonucleotide concentration. Optimal divalent cation concentrations for the desired effect may be determined empirically. The compositions of the invention may further comprise a thermostable DNA polymerase such as Taq DNA polymerase (*Thermus aquaticus*), *Thermococccus litoralis* DNA polymerase, *Pyrococcus furious* DNA polymerase, and the like.

Other embodiments of the invention include oligonucleotide primer extension reactions employing at least one of the subject chimeric phosphoramidate oligonucleotides as primers. In a primer extension reaction, an oligonucleotide primer is annealed, i.e., hybridized, to a site on a polynucleotide template to form a primer-template complex. The primer-template complex is then exposed to an enzyme having DNA polymerase activity (thermostable or otherwise) and to nucleotides (e.g. dATP, dTTP, dGTP, dCTP and/or dideoxynucleotide analogs thereof) in a suitable environment to permit the addition of one or more nucleotide to the primer oligonucleotide at the 3' end of the primer. Examples of oligonucleotide primer extension reactions include chain termination (Sanger) DNA sequencing reactions (Sanger et al, *Proc. Natl. Aca. USA*, 74:5463 (1977)), cycle sequencing (Murray et al, *Nucleic Acids Res.* 17:88–89 (1989)), and PCR (U.S. Pat. Nos. 4,683,195 and 4,683,202). Many types of primer extension reactions employ elevated temperatures in order to denature double-stranded polynucleotides, e.g. PCR and cycle sequencing. In those embodiments of the subject methods employing denaturing temperatures, $Mg^{+2}$ or $Mn^{+2}$ may be added to reduce hydrolysis of the phosphoramidate linkages in the chimeric phosphoramidate oligonucleotides (as described above with respect to the subject compositions).

Another embodiment of the invention is a method of primer extension in which an oligonucleotide primer that may or may not be a chimeric phosphoramidate oligonucleotide according to Formula I is annealed to a template having at least one phosphoramidate linkage. At least one of the phosphoramidate linkages in the template is located at a site other than the site of primer annealing. The annealed primer is then extended across the phosphoramidate linkage or linkages in the template in a DNA polymerase catalyzed primer extension reaction. An example of a primer extension method in which primer extension takes place across a phosphoramidate linkage in a template is PCR in which at least one of the primers is a chimeric phosphoramidate oligonucleotide according to Formula I. In PCR, the phosphoramidate linkages in the chimeric phosphoramidate oligonucleotide primers are part of templates during synthesis of a complementary strand. The ability of phosphoramidate linkage containing polynucleotides to serve as templates in primer extension procedures, including PCR, is extremely surprising. The finding is surprising because of the inability of many DNA analogs to serve as templates in primer extension reactions, e.g., PNAs (peptide nucleic acids, etc.).

Another aspect of the invention relates to the surprising discovery that the chimeric oligonucleotide primers of the invention may be used to suppress non-templated terminal dA (nucleotide) addition to the 3' end of polynucleotide duplexes caused by Taq DNA polymerase during PCR and other primer extension reactions catalyzed by Taq DNA polymerase. Non-templated dA addition is a significant problem in applications requiring accurate determinations of PCR amplification product size, e.g., the use of microsatellite DNA markers (Hu, *DNA and Cell Biology* 12(8):763–770 (1993)). By using chimeric phosphoramidate oligonucleotide primers of the invention in primer extension reactions, the non-templated dA addition catalyzed by Taq DNA polymerase may be suppressed, i.e., reduced, thereby providing for greater accuracy in size determinations of amplification products.

The invention, having been described above, may be better understood by reference to the following examples. The following examples are offered for purposes of illustrating the invention and should not be construed as limitations on the invention.

EXAMPLES

PCR Amplification with Chimeric Phosphoramidate Oligonucleotide Primers

PCR amplification experiments with different combinations of DNA primers, phosphoramidate primers, and chimeric phosphoramidate primers were performed. An 800 base insert between T7 and T3 priming sites was used as a template. The reaction conditions and reagents used are as follows.

Variables in PCR reactions:

A. Buffer and enzymes

1. AmpliTaq with standard Taq buffer

2. AmpliTaq with Tris, pH 9.5 buffer 3. rTth with an XL PCR buffer 4. rTth with new XL PCR buffer B. Cycling conditions (denaturation)

1. 90° C., 5 sec 2. 95° C., 5 sec initial; 90° C. 5 sec all subsequent 3. 92° C., 5 sec 4. 94° C., 5 Ssec then for all: 58° C., 20 sec; 72° C., 2 min for 25 cycles C. Primers 1. T3 standard, T7 standard 2. T3 chimera, T7 standard 3. T3 standard, T7 amidate
4. T3 chimera, T7 amidate The T3 chimera primer is a 19-mer chimeric phosphoramidate oligonucleotide having a block of 10 amidate linkages at the 5' end and a block of 9 phosphodiester linkages at the 3' end. The T7 amidate is oligonucleotide formed completely of phosphoramidate linkages having a 3'-OH terminus.

D. Templates
  1 and 2: both samples with about 800 base PCR product with T3 and T7 primers
All reactions 25 μl, per reaction:

| buffer | (appropriate amount) |
|---|---|
| dNTP's, 1 mM | 3.5 μl |
| T3 primer, 4 μM | 1.0 μl |
| T7 primer, 4 μM | 1.0 μl |
| rTth | 0.5 μl OR |
| Taq, 8 Units /μl | 0.25 μl |
| diH2O | quantity sufficient to produce a final volume of 25 ml |

All combinations of variables done=128 reactions
Results:
All PCR reactions with primers 1 and 2 worked. No PCR reactions with primers 3 and 4 worked. Generally, primers 2 gave more PCR product than primers 1.5 μl each reaction was loaded on gel.

Subsequent sequencing of PCR products showed good sequencing of all PCR products made with primers 1 or 2 and no sequencing from PCR products made with primers 3 or 4.

Some of the above PCR products were sequenced with the T7 amadate or T3 chimera oligos. The T3 chimera gave good sequence data, comparable to or better than that from the standard T3 primer. The amidate T7 oligo gave no sequence data. All reactions were done using standard dye terminator chemistry.

Incorporation by Reference
All papers and documents (including patents) referenced in this specification are incorporated herein by reference.
Equivalents While the invention has been described with reference to specific methods and embodiments, it will be appreciated that various modifications and changes may be made without departing from the invention. These and other equivalents are intended to be covered by the following claims.

What is claimed is:

1. A chimeric oligonucleotide primer according to the formula

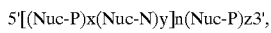

wherein n≧1[0], x≧0, y≧1, and z≧1, and wherein the primer is of sufficient length to hybridize to a polynucleotide template of interest.

2. An oligonucleotide according to claim 1, wherein z is at least 3.

3. An oligonucleotide according to claim 1, wherein the oligonucleotide is at least 5 bases in length.

4. A composition comprising an oligonucleotide according to claim 1 and a divalent cation, wherein the cation is present in a concentration sufficient to reduce hydrolysis of the chimeric oligonucleotide or increase the stability of a duplex formed between the oligonucleotide and polynucleotide.

5. A composition according to claim 4, wherein the divalent cation is selected from the group consisting of $Mn^{+2}$ and $Mg^{+2}$.

6. A composition according to claim 1, further comprising a thermostable DNA polymerase.

7. A composition comprising a thermostable DNA polymerase and a chimeric oligonucleotide primer according to the formula

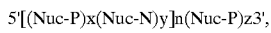

wherein n≧1, x≧0, y≧1, and z≧1, and wherein the primer is of sufficient length to hybridize to a polynucleotide template of interest.

* * * * *

UNITED STATES PATENT AND TRADEMARK OFFICE
CERTIFICATE OF CORRECTION

PATENT NO. : 6,043,070
DATED : March 28, 2000
INVENTOR(S) : Ellis et al.

It is certified that error appears in the above-indentified patent and that said Letters Patent is hereby corrected as shown below:

On the title page: Item [56]

*Attorney, Agent, or Firm* - "Scott R. Bartner" should read
-- Scott R. Bortner --.

Column 8, line 13 - "wherein $n \geq 1[0]$, $x \geq 0$, $y \geq 1$, and $z \geq 1$ and wherein the" should read
-- wherein $n \geq 1$, $x \geq 0$, $y \geq 1$, and $z \geq 1$ and wherein the --.

Signed and Sealed this

Thirteenth Day of March, 2001

Attest:

NICHOLAS P. GODICI

Attesting Officer
Acting Director of the United States Patent and Trademark Office